United States Patent [19]
Hoefer et al.

[11] 4,224,134
[45] Sep. 23, 1980

[54] VERTICAL GEL SLAB ELECTROPHORESIS APPARATUS AND METHOD THEREFOR

[75] Inventors: Peter S. Hoefer, San Francisco; Michael Whitesides, Daly City, both of Calif.

[73] Assignee: Hoefer Scientific Instruments, San Francisco, Calif.

[21] Appl. No.: 714

[22] Filed: Jan. 3, 1979

[51] Int. Cl.$^2$ .................. G01N 27/26; G01N 27/28
[52] U.S. Cl. ........................... 204/299 R; 204/180 G
[58] Field of Search ................. 204/180 G, 299 R; 23/230 B; 424/12

[56] References Cited

U.S. PATENT DOCUMENTS

| | | | |
|---|---|---|---|
| 3,129,158 | 4/1964 | Raymond et al. | 204/180 G |
| 3,902,986 | 9/1975 | Nees | 204/180 G X |
| 4,035,377 | 7/1977 | Detroy | 204/180 G X |
| 4,142,960 | 3/1979 | Hahn et al. | 204/180 G X |

*Primary Examiner*—Arthur C. Prescott
*Attorney, Agent, or Firm*—Flehr, Hohbach, Test, Albritton & Herbert

[57] ABSTRACT

A vertical gel electrophoresis apparatus includes a U-shaped structure consisting of a container for upper buffer solution and extending parallel plate sample units which form the legs of the U. In the casting mode the U-shaped structure is inverted with the tank resting on the ground surface and with the bottom ends of the sample units being sealed against the sealing strip on the top of the container. After the sample units are filled to the top and the gel polymerized (with the use of a comb-like well forming structure if needed) the sample units are flipped and reinserted. However because of the offset of the plates of the sample units in the lateral direction the formerly sealed end of the sample plates is now exposed to a slot or aperture which extends into the upper buffer solution container. The entire U-shaped structure rests in a tank of lower buffer solution on a slab type heat exchanger where cooling can occur on both sides of the sample units.

5 Claims, 6 Drawing Figures

VERTICAL GEL SLAB ELECTROPHORESIS APPARATUS AND METHOD THEREFOR

The present invention is directed to a vertical gel slab electrophoresis apparatus and method therefor.

When carrying out the process of gel electrophoresis, it is necessary to first fill the sample unit with gel and secondly apply an appropriate voltage to cause electrophoretic separation of the sample within the gel slab.

To accomplish the above, application of a voltage to upper and lower conductive buffer solutions which respectively contact both end slots of the sample unit is necessary. These buffer solutions, because of the potential between them, are separated into isolated compartments by several different techniques. One is illustrated in U.S. Pat. No. 3,980,540 in the name of Stanton A. Hoefer, assigned to the present assignees. In this foregoing patent the first step of filling the sample unit is conducted by placing a rubber seal against the bottom slot of the sample unit and then injecting gel through the bottom seal by means of a hypodermic needle. The seal is then removed from the bottom of the plate by a camming arrangement where the plate remains stationary and the seal itself is lowered in order to expose the bottom slot to a buffer solution.

The foregoing two-step process of first filling the sample unit with gel and secondly, with the use of a buffer solution, supplying the voltage across the sample unit and the concomitant required electrical isolation of the buffer solution, can lead to complex apparatus or operational set-ups for which simplification is always desirable from an operator's standpoint.

It is therefore an object of the present invention to provide an improved vertical gel slab electrophoresis apparatus and method therefor.

In accordance with the above object there is provided such apparatus which comprises a container for a conductive buffer solution and including a longitudinal sealing strip. A sample unit includes a pair of spaced plates for containing gel and with open top and bottom slots. Means are provided for retaining the sample unit in one orientation for sealing a slot against the strip and another orientation where such slot is exposed to a buffer solution.

From a method standpoint there is provided a vertical gel slab electrophoresis method using as a sample unit a pair of spaced plates which is filled with gel in a casting mode and with open top and bottom slots for contacting upper and lower buffer solutions across which a separating voltage is applied in an operational mode. Also included are support means for sealing the bottom slot in a casting mode and exposing both slots to the buffer solutions in the operational mode. The method comprises the steps of inserting an empty sample unit into the support means with the bottom slot of the unit being sealed. Gel is placed in the unit through its open top slot. Thereafter such unit is removed from the support means and reinserted so that both top and bottom slots are exposed. Finally, the top and bottom slots of the unit which has been filled with gel are placed in liquid contact with the upper and lower buffer solutions.

Figure 1:
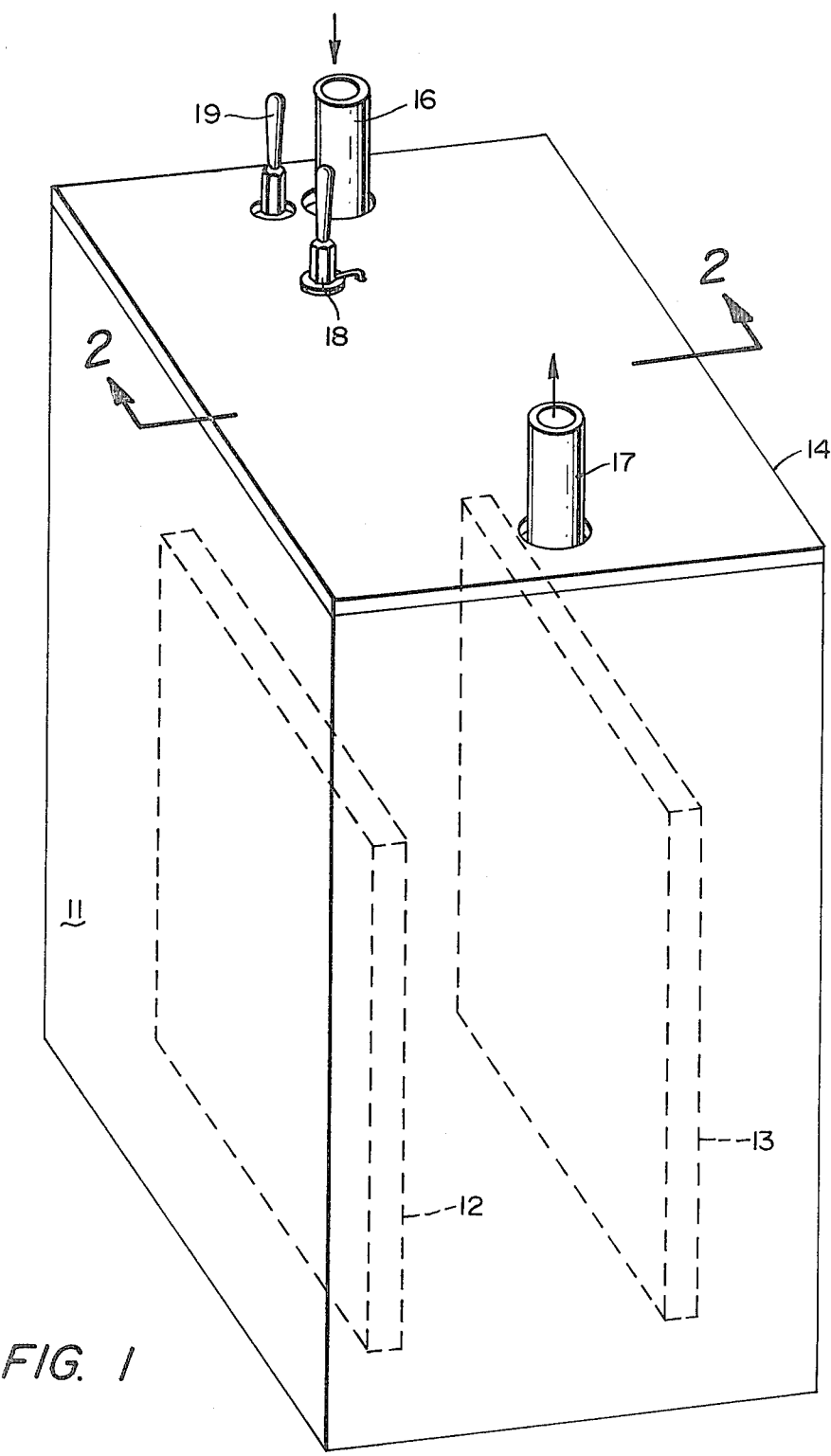
FIG. 1 is a perspective view of a slab electrophoresis unit embodying the present invention.

FIG. 1 illustrates the overall vertical gel slab electrophoresis unit of the present invention. It includes a lower buffer solution tank or container 11 holding a pair of sample units 12 and 13 containing gel which are shown in dashed-outline and will be described in detail below. Container 11 has a top 14 having two apertures for the heat exchanger or coolant tubes 16 and 17. In addition, means for applying an electrical voltage across the buffer solutions to produce the electrophoresis effect consists of one terminal 18 mounted on top 14 and a second terminal 19 extending through an aperture in the top.

In general, in the casting mode gel is polymerized along with the formation of suitable sample wells, in sample units 12 and 13. Then in the operating mode a voltage is applied across terminals 18 and 19 to place an electric field across the top and bottom of the respective sample units 12 and 13 to cause electrophoretic separation.

Figure 2:
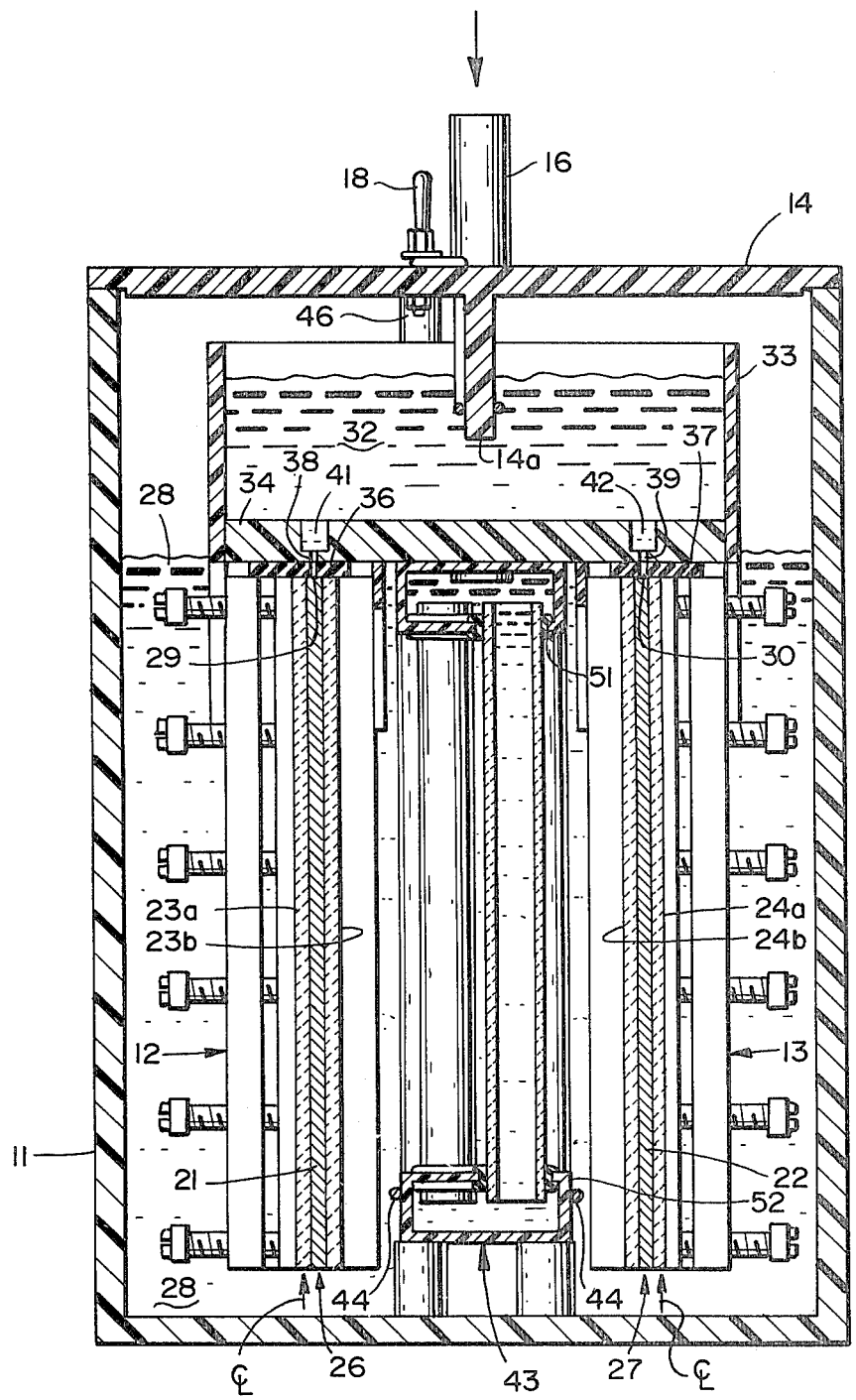
FIG. 2 is a detailed cross-sectional view taken along the line 2—2 of FIG. 1.

FIG. 2 best illustrates this operational mode, the cross-section of FIG. 1 illustrating the sample units 12 and 13 which contain polymerized gel 21, 22, respectively, between pairs of spaced rectangular glass plates 23a, 23b and 24a, 24b. Each pair of plates 23, 24 has a bottom slot 26, 27 which makes liquid contact with the conductive buffer solution 28, in partially filled tank 11 and a top slot 29 and 30 which are in liquid communication with conductive upper buffer solution 32 which is in the container 33.

More specifically, the bottom 32 of container 33 has fastened to it a pair 36, 37 of longitudinal sealing strips constructed of resilient material each of which has an elongated aperture 38, 39 which as illustrated in FIG. 2 mate with the slots 29 and 30. Apertures 38, 39 lead through into the container 33 by means of apertures 41 and 42 in bottom 34. The top portion of apertures 41 and 42 are enlarged so that two-dimensional electrophoresis may be carried on by laying a tube gel in the enlarged portion. This is of course done with the top 14 off and no upper buffer liquid 32 in place. It is obvious that there is ample room to insert the tube gel.

Upper buffer solution 32 makes electrical contact with terminal 18 through top 14 which on its extension 14a carries an electrode, connected to terminal 18, which would be normally immersed in the buffer solution 32.

As is apparent (and also referring to FIG. 3 briefly) container 33 and its downwardly extending sample units 12 and 13 form a U-shaped structure of which the container is the upper bight portion and the sample units 12 and 13 are the legs of the U. The bight portion, by way of its bottom 34, is supported by the heat exchanger or cooling unit 43 which is illustrated in greater detail or better perspective in FIG. 6. Heat exchanger 43 has on its lower portion a loop conductor 44 which makes electrical contact with the lower buffer solution 28 and is electrically connected to terminal 19 by a convenient vertical support post extension 46 of the heat exchanger unit 43. (See FIG. 6 again.)

Figure 6:
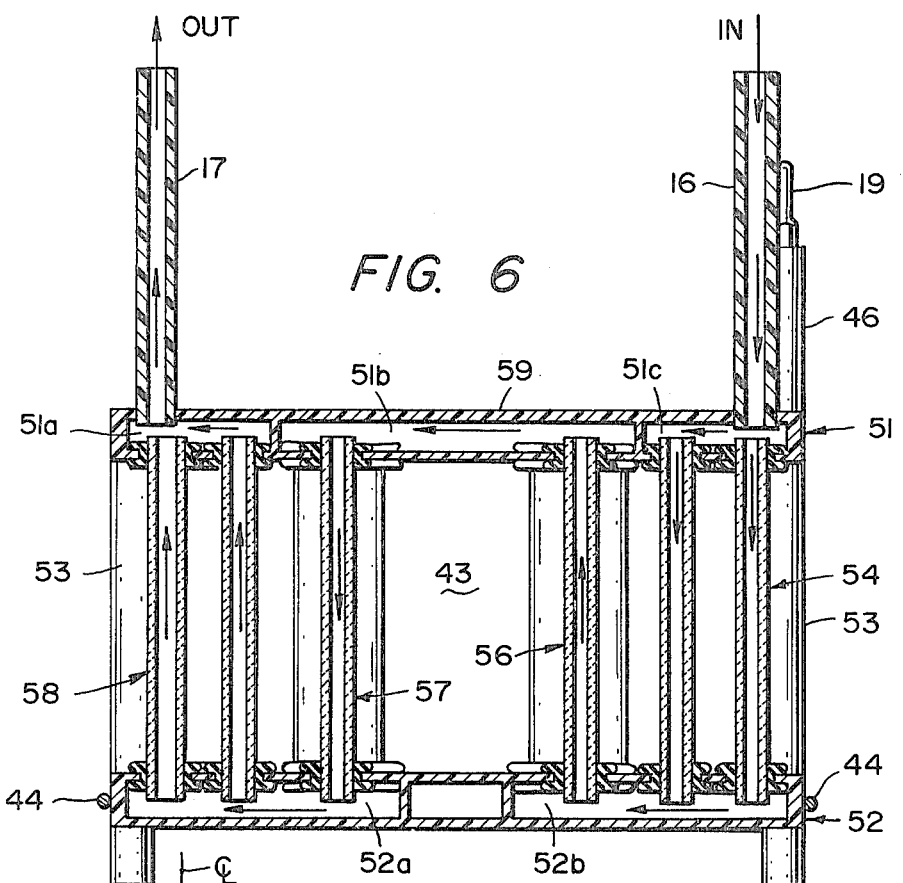
FIG. 6 is a cross-sectional view of a heat exchanger portion of FIG. 2.

Heat exchanger 43 as shown in greater detail in FIG. 6 in fact provides a serpentine path in a vertical plane for the cooling liquid as it travels from the input 16 to the output 17. That is provided by combination of a top manifold 51 and a bottom manifold 52 which are held together by vertical posts 53. Top manifold 51 has three compartments 51a, 51b and 51c. Bottom manifold 52 has compartments 52a and 52b. A center aperture can be used for a magnetic stirrer if desired. To provide for the cooling effect clusters of three tubes 54 connect manifold portion 51c to 52b. Tube cluster 56 connects 52b to 51b. Cluster 57 connects 51b to 52a. And lastly, three-tube cluster 58 connects manifold 52a to 51a and thence to the outlet tube 17. By the use of a serpentine path and the cluster of three tubes a large cooling area is provided for the lower buffer solution 28. Referring to FIG. 2 it is also apparent that the lower buffer solution is in full contact with both plates 23a, 23b and 24a, 24b so that effective cooling or temperature regulation is provided for both sides of each sample unit.

As discussed before, the U-shaped structure of FIG. 2 formed by container unit 33 and the sample units 12 and 13 rests on the top surface 59 of manifold 51 between an outlet tube 16 and 17. Thus the length of the sample units in a vertical direction can be increased merely by lengthening the support posts 53 of the heat exchanger 43 (and of course also deepening the tank 11).

Figure 3:
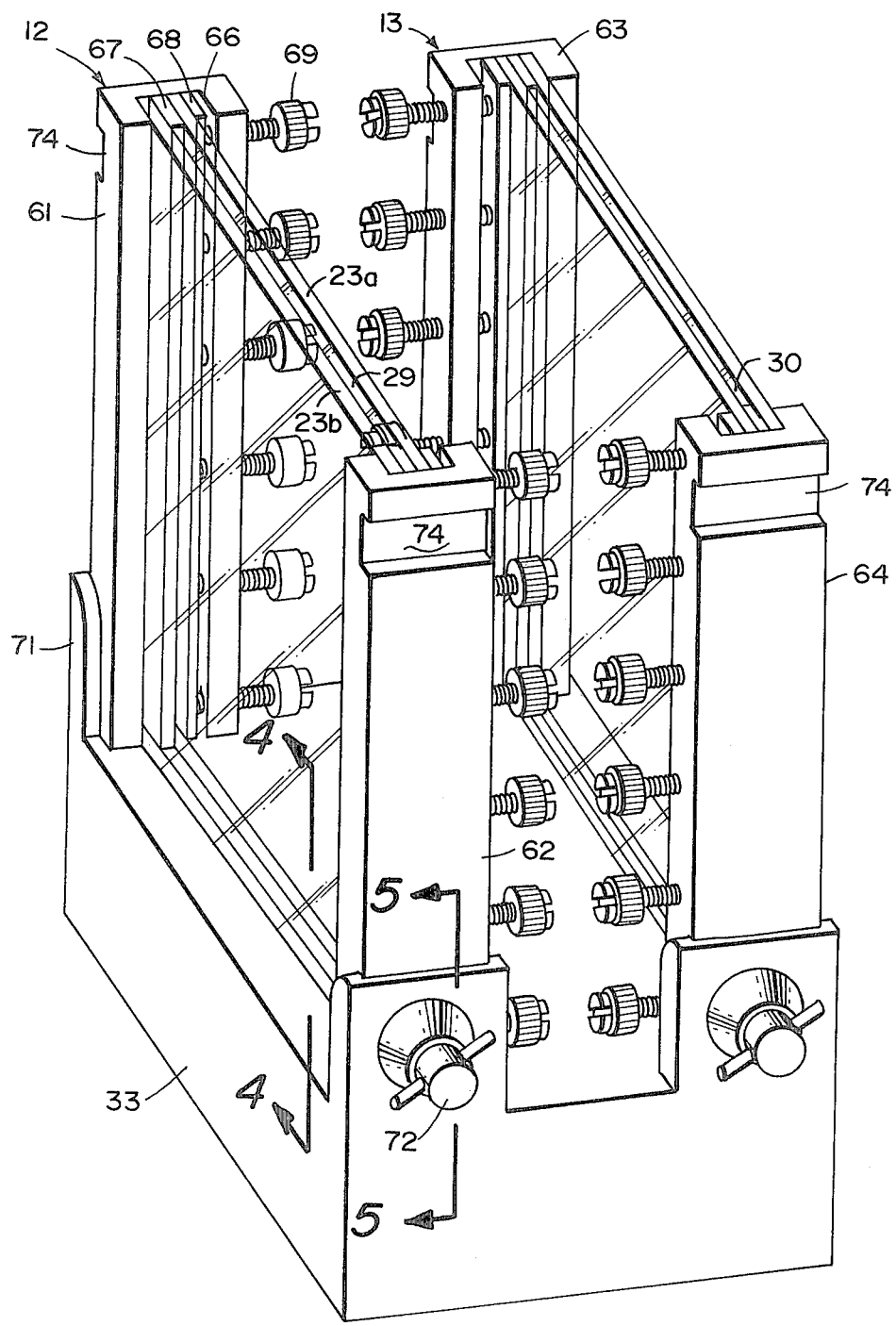
FIG. 3 is a perspective view of an interior portion of FIGS. 1 and 2 which has been flipped.
Figure 4:
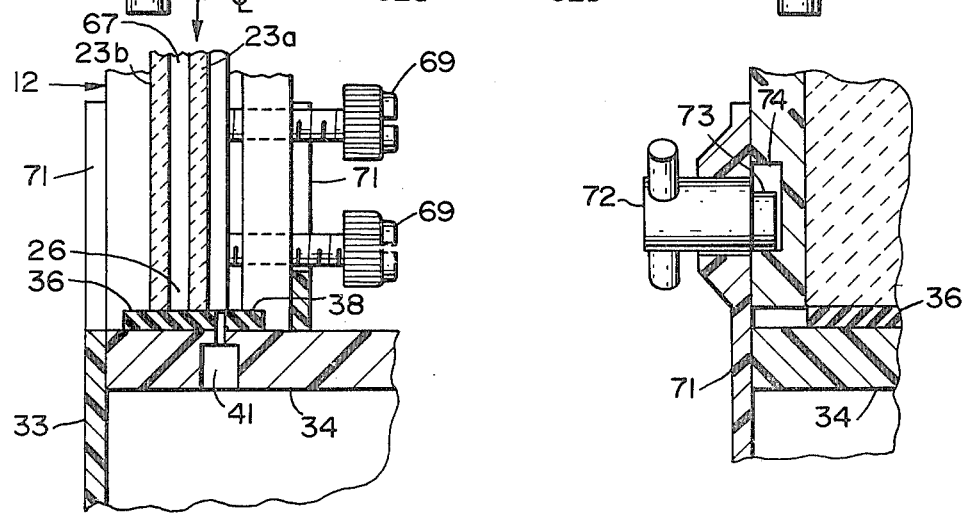
FIG. 4 is an enlarged cross-sectionl view taken along the line 4—4 of FIG. 3.

FIG. 3 illustrates the U-shaped structure of FIG. 2 removed from tank 11 and inverted. Thus container 33 now serves as the base for sample units 12 and 13. This is done during the casting mode where the gel is placed through the open top slot 29 in the case of sample unit 12, and 30 in the case of sample unit 13. It is therefore apparent that the orientation of sample units 12 and 13 in this casting mode have been shifted and that both units have in essence been rotated about their horizontal axis 180°. In other words, referring to FIG. 4, slot 26 is now against the sealing strip 36 whereas in FIG. 2 it was exposed to buffer solution 28. In the casting mode when the gel is placed in the sample unit the bottom of the sample unit must of course be sealed. Thereafter when the gel is polymerized the seal can be removed in the operational mode proceeded with where both ends of the gel are exposed to a voltage difference to provide for the electrophoresis. However, in accordance with the invention the sealed casting mode is provided by reason of the fact that by changing orientation of the sample units 12 and 13 (i.e. flipping) and the fact that the sample units have a centerline from which the pair of plates 23a, 23b and 24a, 24b are offset. This allows the sample units to be filled as illustrated in FIGS. 3 and 4, the sample units removed, either flipped or rotated along the vertical axis by 180° and reinserted to retake the position shown in FIG. 2. This is of course where the slots 29 and 30 mate with apertures 38 and 39 of the bottom 34 of the upper buffer solution container 33.

If no sample wells are desired but rather a two-dimensional electrophoresis carried on by the use of enlarged portions 41 and 42 of the bottom 34 of tank 33 as illustrated in FIG. 2, then of course the sample units need only be rotated along their vertical axis by 180° since no comb type well forming structure need be used.

Although not illustrated specifically in FIG. 3 a common technique in the casting mode is to provide a comblike plastic structure which would be inserted in the slots 29 and 30 during the polymerization of the gel so as to form a number of vertical sample wells. Thereafter in order to position these sample wells with the appropriate apertures in the upper buffer solution tank 33, sample units 12 and 13 must be flipped about their horizontal axis. This is quite apparent where the retaining screws for the sample plates in FIG. 2 are outwardly pointing and in FIG. 3 inwardly pointing.

Figure 5:
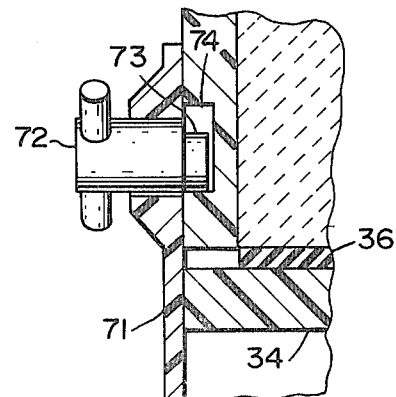
FIG. 5 is an enlarged cross-sectional view taken substantially along line 5—5 of FIG. 3.

Now referring to the detailed construction of the sample units which is also illustrated in FIGS. 4 and 5, each sample unit includes a pair of vertical guides 61, 62 in the case of unit 12, and 63, 64 in the case of unit 13. Each guide has an internal groove, for example 66 in the case of guide 61, in which is located in sequence a glass plate 23b, a spacer 67 which determines the thickness of the gel, glass plate 23a and a final spacer 68 against which a screw 69 presses. Thus, referring to FIG. 4 where the centerline is indicated coinciding with plate 23a, the offset nature of the glass plates is quite apparent. And of course this lateral offset allows for the changing orientation of the sample units to provide both a casting mode and an operational mode with basically the same common structure.

Sample units 12 and 13 (referring again to FIG. 3 and now FIG. 5) are held into place by the channels 71 extending from container 33 illustrated in FIG. 5. At the end of the channel 71 is a cam unit 72 which has an off-center nub 73 which mates with a horizontal channel 74 which is located at the upper and lower portion of each guide rail 61, 62, 63 and 64. As illustrated in FIGS. 4 and 5 when the cam 72 is rotated in one direction or the other it will press the pair of glass plates onto the sealing strip 36.

Thus an improved vertical gel slab electrophoresis apparatus and method therefor has been provided.

what is claimed is:

1. Vertical gel slab electrophoresis apparatus comprising: a container for a conductive buffer solution and including a longitudinal sealing strip, a sample unit including a pair of spaced plates for containing gel and with open top and bottom slots; common means for retaining said sample unit in one orientation for sealing a slot against said strip to allow gel to be cast, and another orientation where said slot is displaced from said strip and exposed to a buffer solution to allow for electrophoresis.

2. Apparatus as in claim 1 where said sample unit has a vertical centerline and said pair of spaced plates are laterally offset from said centerline.

3. Vertical gel slab electrophoresis apparatus comprising: a conductive lower buffer solution tank; a slab type heat exchanger extending down the middle of such tank; a U-shaped structure with a bight portion supported by said heat exchanger and forming an upper buffer solution container and with the downwardly extending legs being a pair of gel containing sample units, each with a bottom slot in liquid communication with said lower buffer solution and an upper slot in fluid communication with said upper buffer solution.

4. Apparatus as in claim 3 including pairs of cam means for retaining each of said legs against said bight portion of said U-shaped structure.

5. Apparatus as in claim 3 where said heat exchanger includes a serpentine path in the vertical plane for the heat exchanging liquid.

* * * * *